United States Patent [19]
Yankielun et al.

[11] Patent Number: 5,784,338
[45] Date of Patent: Jul. 21, 1998

[54] TIME DOMAIN REFLECTOMETRY SYSTEM FOR REAL-TIME BRIDGE SCOUR DETECTION AND MONITORING

[75] Inventors: Norbert E. Yankielun, Lebanon, N.H.; Leonard J. Zabilansky, Perkinsville, Vt.

[73] Assignee: The United States of America as represented by the Secretary of the Army, Washington, D.C.

[21] Appl. No.: 929,801

[22] Filed: Sep. 15, 1997

[51] Int. Cl.⁶ .................................................. H04B 17/00
[52] U.S. Cl. ................................................ 367/131; 367/13
[58] Field of Search ................... 367/131, 13; 73/304 R; 405/73; 33/719; 342/22; 324/533, 71.2

[56] References Cited

U.S. PATENT DOCUMENTS

| | | | |
|---|---|---|---|
| 2,707,267 | 4/1955 | Gavin | 324/533 |
| 3,617,996 | 11/1971 | Herbert | 367/105 |
| 3,686,887 | 8/1972 | Bruce | 405/74 |
| 3,727,128 | 4/1973 | McFerrin | 324/533 |
| 3,991,364 | 11/1976 | Wiznerowicz | 324/533 |
| 4,855,966 | 8/1989 | Cinquino | 367/99 |
| 4,914,394 | 4/1990 | Meyer | 324/534 |
| 5,032,794 | 7/1991 | Ridd et al. | 73/304 R |
| 5,361,776 | 11/1994 | Samuelson et al. | 600/547 |
| 5,479,724 | 1/1996 | Nahajski et al. | 73/290 R |
| 5,532,687 | 7/1996 | Richardson et al. | 340/870.33 |
| 5,554,936 | 9/1996 | Mohr | 324/642 |

*Primary Examiner*—Daniel T. Pihulic
*Attorney, Agent, or Firm*—Luther A. Marsh

[57] ABSTRACT

An apparatus for detecting and monitoring scouring around a structural member uses time-domain reflectometry (TDR) to measure the level of sediment around the submerged portion of a structural member such as a bridge pier, dock, utility crossing, or similar structure. The apparatus includes an electrical pulse generator which transmits a series of electrical pulses, a sensor which is connected with the pulse generator, and a signal analyzer which receives and interprets the portion of the electrical pulses reflected back to the source from an interface, such as water/air or water/gravel, to calculate the position of the interface along the sensor. Knowledge of the position of the interfaces before and after a scouring event and of the dielectric constants of the surrounding media allows the user to detect and monitor the level of erosion caused by scouring.

11 Claims, 2 Drawing Sheets

TIME DOMAIN REFLECTOMETRY SYSTEM FOR REAL-TIME BRIDGE SCOUR DETECTION AND MONITORING

BACKGROUND OF THE INVENTION

The present invention relates to a bridge scour detection and monitoring apparatus and, more particularly, to a time domain reflectometry (TDR) system for real-time detection and monitoring of sediment levels around the submerged foundation of a structural member such as a bridge.

Bridge scour is a severe problem that costs millions of dollars in terms of damage, loss of life, and required annual maintenance by leaving infrastructure, including bridge piers and docks, in unsafe conditions. A scouring event occurs during times of rapid river flow and icing conditions when sediment, including rocks, gravel, and silt is transported by river currents away from bridge piers and similar structures. Scour is dynamic, and ablation and deposition can occur within and event, so the net effect cannot be easily predicted. If the event is severe enough, foundation material below the pier footing may erode, leaving the structure unsupported and in jeopardy of collapse. Measurement of scour is therefore useful in monitoring stability and repair needs for bridges and other waterway structures before major damage occurs.

BRIEF DESCRIPTION OF THE RELATED ART

Currently, there are several techniques and devices used for detecting and monitoring scour, including subsurface interface radar, transducers, optical fathometers, physical probes, and visual inspection. All of these devices suffer from significant drawbacks.

Radar has been successfully employed to bathymetrically determine scour conditions. The technique is usually used after an event, indicating the final status of the sedimentation surrounding a pier. Sonar techniques have been similarly employed. Neither of these techniques are continuously employed in situ during a scour event and both require skilled operators to perform the test and interpret the results.

Neutral buoyancy sensors or "fish" equipped with a seismic transducer and a radio transmitter have been anchored at varying depths in the sediments around bridge piers (Zabilansky, L. J., *Ice Force and Scour Instrumentation for the White River*, Cold Regions Research and Engineering Laboratory, Hanover, N.H., Special Report 96-6, April 1996). As the fish are uncovered by the scouring process they are moved by the currents and they transmit signals to a receiver located on the shore to indicate that the scour has reached their tethered depth. When the sediment is redeposited, the fish are then re-buried at approximately their original depth. While this system is re-settable, it still gives a fairly crude spatial indication of the scour progression. Also, the fish are battery powered and thus have a limited life and must be replaced periodically.

Various devices are known in the patented prior art for detecting and monitoring scouring. The U.S. Pat. No. 4,502,044, to Cinquino for example, discloses a method and apparatus for monitoring bridge structures for scouring having apparatus for determining the distance between the topmost portion of the soil bed and one or more fixed points on a pier. In one embodiment of the invention, the distance determining apparatus comprises a sonar device for determining the distance between the soil bed and a fixed point on the pier.

The U.S. Pat. No. 3,617,996 to Herbert discloses an apparatus for scour detection at bridge piers and the like utilizing a plurality of electroacoustical transducers mounted on the structure to measure the effects of scouring on the soil bed adjacent to the structure.

Scouring measurement and detection utilizing time domain reflectometry (TDR) has been suggested in the literature (Dowding, C. H. and Pierce, C. E., *Use of Time Domain Reflectometry to Detect Bridge Scour and Monitor Pier Movement*, United States Department of Interior Bureau of Mines, Symposium and Workshop of Time Domain Reflectometry in Environmental, Infrastructure and Mining Applications, Northwestern University, Illinois, Sep. 7–9, 1994). However, such systems differ from the present invention in that they employ a sacrificial sensor buried vertically in the sediment. Once a section of the sensor is exposed by scouring, the current causes the exposed section to be broken off, therefore shortening the sensor. This shortening of the sensor can then be detected and measured by an on-shore instrument. The drawback to this technique is that the sacrificial sensor, which is destroyed in the measurement process, must be replaced after every event.

The present invention was developed in order to overcome these and other drawbacks of the prior devices by providing a bridge scour detection and monitoring device which takes advantage of time domain reflectometry (TDR) technique for real-time measurement of sediment levels around a submerged structural member. The principle of TDR is widely known and applied to numerous measuring and testing applications. TDR operates by generating an electromagnetic pulse (or a fast rise time step) and coupling it to a transmission line. The pulse propagates down the transmission line at a fixed and calculable velocity which is a function of the speed of light in addition to the electrical and physical characteristics of the transmission line. The pulse will propagate down the transmission line until it reaches the end of the line where it will be reflected back towards the source. The time t in seconds that it takes for the pulse to propagate down and back the length of the transmission line is called the "round trip travel time" and is calculated as:

$$t = 2L/v$$

where:
L=length of a parallel metal rod sensor (m)
v=velocity of propagation (m/s)
The velocity of propagation can be given as:

$$v = c/(E^{1/2}) = c/n$$

where:
c=velocity of light in free space ($3 \times 10^8$ m/s)
E=the relative dielectric constant of the media surrounding the transmission line
n=index of refraction of the media surrounding the transmission line.

In the case of a two wire parallel transmission line, changes in the dielectric media in the immediate surrounding volume will cause a change in the round trip travel time. Freshwater has a dielectric constant E of 80, ice has a dielectric constant of 3.17, and dry sedimentary materials (e.g.: soil, gravel and stone) have dielectric constants in the range of 5 to 8. Wet sediment has a dielectric constant which is a mixture of those of water and dry soil. The dielectric constant E of this mixture will vary depending upon the local sedimentary material constituency, but in all cases the bulk dielectric (bulk index of refraction) of the mixture will be less than that of water alone and significantly greater than that of the dry sedimentary materials.

At any interface along the transmission line such as at an air/water interface or a water/sediment interface, a dielectric discontinuity exists. As a pulse traveling down the transmission line encounters the air/water interface, a portion of the pulse energy is reflected back to the source by the interface while the remaining portion of the energy will continue to propagate through the interface until the pulse encounters another interface or the end of the transmission line where all or part of the remaining pulse energy is reflected back along the transmission line to the source.

The series of reflected pulses form a signature signal which a signal analyzer interprets to calculate the position of the interfaces along the transmission line as a function of the time elapsing between the reflected pulses and dielectric constants of the surrounding media. Knowledge of the positions of the interfaces over a period of time allows the user to detect and monitor the level of erosion caused by scouring.

SUMMARY OF THE INVENTION

Accordingly, a primary object of the present invention is to provide a real-time bridge scour detection and monitoring system which uses time-domain reflectometry (TDR) to measure the level of sediment around the submerged portion of a structural member such as a bridge pier, dock, utility crossing, or the like. The apparatus includes an electrical pulse generator which transmits a series of electrical pulses, a sensor which is connected with the pulse generator, and a signal analyzer which receives and interprets the portion of the electrical pulses reflected back to the source from an interface, such as water/air or water/gravel.

It is another object of the invention to provide a bridge scour detection and monitoring system that is built with relatively inexpensive instrumentation hardware and uses a robust permanent sensor arrangement which may be economically and easily deployed.

It is another object of the invention to provide a bridge scour detection and monitoring system with a real-time computer algorithm to compare an initial reference set of interface positions with a subsequently measured set of positions and to trigger an alarm when a significant change is observed in the TDR signature or when a difference in the position of interfaces over time exceeds a predetermined threshold.

It is a further object of the invention to provide a bridge scour detection and monitoring system having minimal user interface, simple installation, and low maintenance due in part to the fact that the system has no moving or mechanical components.

BRIEF DESCRIPTION OF THE DRAWINGS

Other objects and advantages of the invention will become apparent from a study of the following specification when viewed in light of the accompanying drawings, in which.

DETAIL DESCRIPTION

Figure 1:
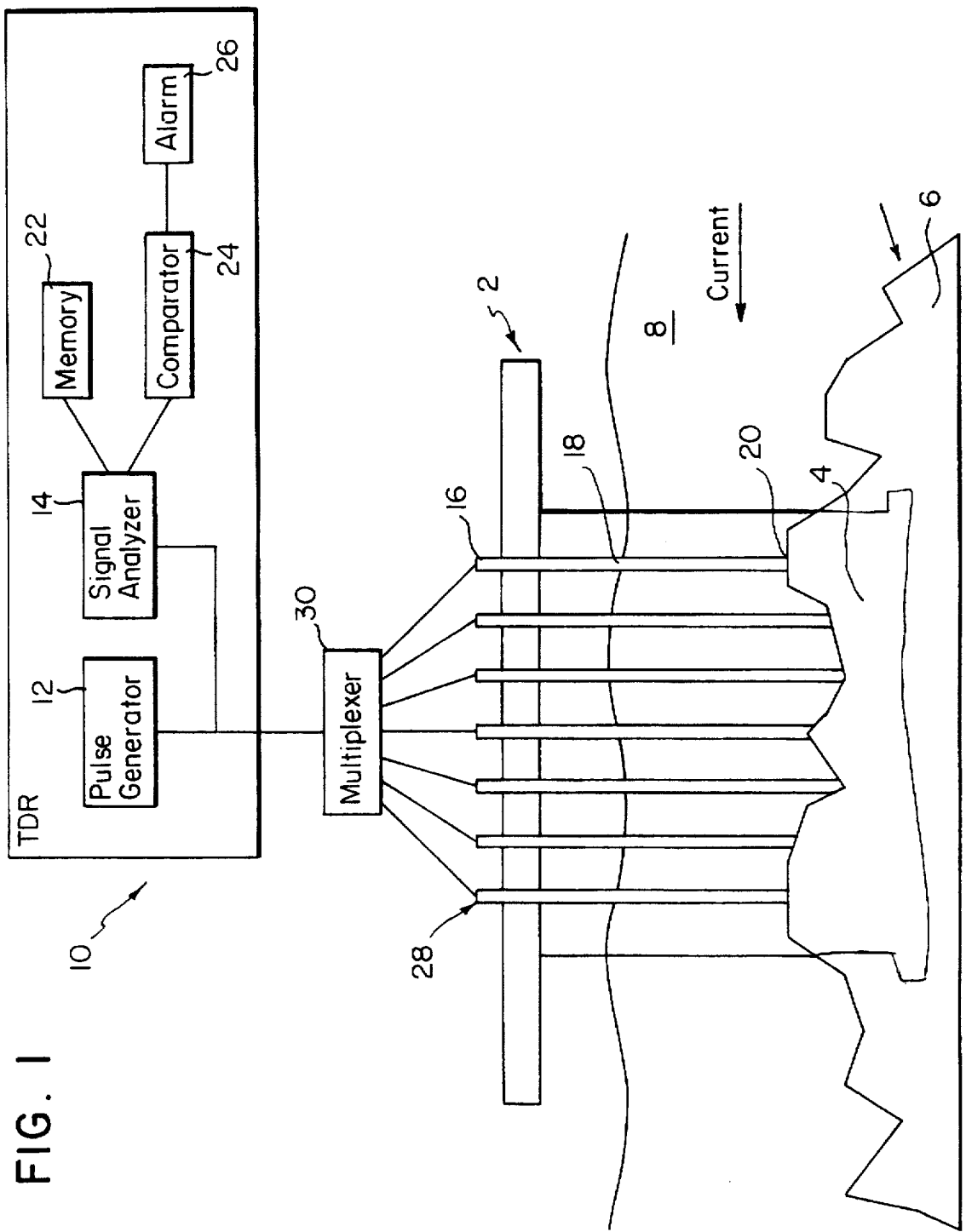
FIG. 1 is a schematic view of a structural member having a sensor comprised of parallel transmission lines multiplexed to a single pulse generator and signal analyzer according to the invention.

Referring now to FIG. 1, there is shown a structural member 2 having a lower portion 4 arranged in sediment 6 submerged beneath a body of water 8. A time domain reflectometry (TDR) device 10 is used to measure the scouring around the structural member 2. The device 10 includes an electric pulse generator 12, a signal analyzer 14 connected with the pulse generator 12, and a set of parallel transmission lines 16 also connected with the pulse generator 12 which extend downwardly from above the water line to the lower portion 4 of the structural member 2. To take a scouring measurement, an electrical pulse is sent down the transmission lines 16 by the pulse generator 12. Portions of the propagated pulses are reflected back from the air/water interface 18 and water/sediment interface 20, respectively, where they are received by a signal analyzer 14 which interprets the reflected pulses to calculate the position of each interface along the transmission line 16. For any particular structural member or set of structural members, it will be obvious to strategically employ as many detectors as needed to accurately and efficiently measure scouring.

Following installation of the system at a particular structural member, an initial reference measurement of the interface positions along each transmission line 16 is taken by propagating an electric pulse along the line with the TDR device 10. This initial reading is stored in a memory 22, which is included in the signal analyzer 14. Subsequent measurements of sets of interface positions are frequently or automatically taken and stored in the memory 22 to record the position of the sediment 6 level as a result of scouring over time. A comparator 24 is also included as part of the signal analyzer 14 to calculate the change over time in the measurement of the interface positions between the initial reference set of interface positions and subsequently measured sets of interface positions. The comparator 24 can use a real-time computer algorithm to compare multiple measurements of interface positions and also may trigger an alarm 26 when a significant change is observed or when a predetermined threshold difference between measurements of interface positions is exceeded.

The system can also be configured so that the TDR instrument 10 is detachably connected to the parallel transmission lines 16 so that they may be periodically, i.e., monthly, transported to a structural site and manually interfaced to each of the transmission lines 16. By sharing the TDR instrument 10 among numerous infrastructure sites, further economy of operation can be gained.

Alternatively, a single TDR instrument 10 can be used in conjunction with a sensor 28, formed of numerous transmission lines 16 by inserting a multiplexer 30 between the sensor 28 and the TDR instrument 10. In this configuration, pairs of parallel transmission lines 16 are positioned at areas of interest along a structural member 2 and the multiplexer 30 automatically and electronically multiplexes the numerous pairs of parallel transmission lines 16 into a single TDR 10.

Figure 2:
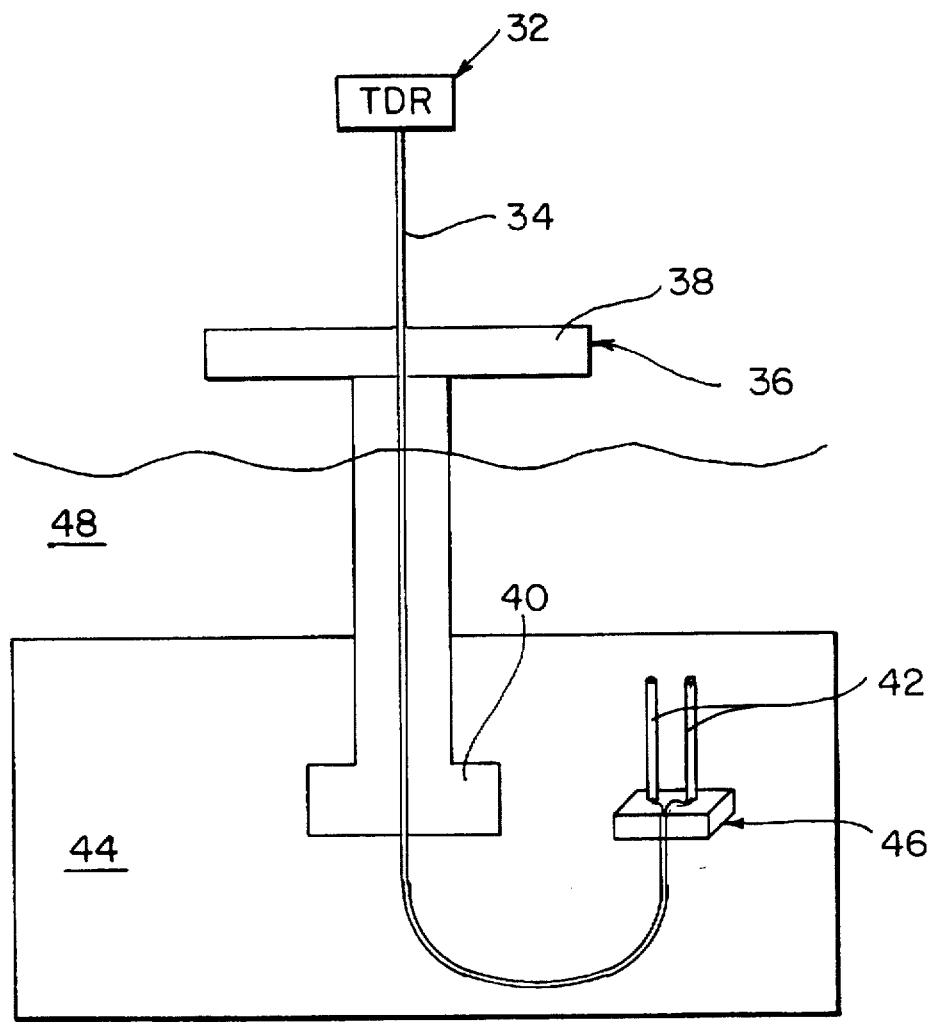
FIG. 2 is a schematic view illustrating the placement of a coaxial cable and robust transmission lines according to an alternate embodiment of the invention.

Referring now to the configuration shown in FIG. 2, a TDR instrument 32 is connected to a coaxial transmission line 34 that is routed downwardly within a structural member 36 from an upper portion 38 arranged above the water surface, to a lower portion 40 buried in the floor of the body of water. The coaxial transmission line 34 exits the lower portion 40 and is connected to a sensor comprising a robust set of vertical transmission lines 42 that extend adjacent to the lower portion 40 and vertically upward into the surrounding sediment 44 from a secure base 46. As scouring occurs and the sediment 44 erodes, the transmission lines 42 are exposed to the surrounding water 48 which cause an interface to form along the transmission lines 42. The position of the developing interface along the transmission lines 42 can be measured to determine the progression of the scouring. A later scouring event may result in a favorable re-shifting of sediment 44 that will re-bury the transmission lines 42 where they will rest until the next scouring event.

While in accordance with the provisions of the Patent Statutes the preferred forms and embodiments of the invention have been illustrated and described, it will be apparent to those of ordinary skill in the art that various changes and modifications may be made without deviating from the inventive concepts set forth above.

What is claimed is:

1. Apparatus for monitoring scouring around a structural member having a lower portion buried in the floor of a body of water, a submerged portion, and an upper portion arranged above the water surface, comprising:

(a) pulse generator means arranged above the water surface for generating a plurality of electromagnetic pulses;

(b) sensor means connected with said pulse generator means and arranged adjacent the lower portion of the structural member, said sensor means comprising at least one pair of parallel transmission lines which receive and reflect said pulses, said reflected pulses being a time-domain function of the properties of the surrounding media through which said sensor means passes;

(c) signal analyzer means connected with said sensor means for receiving and analyzing said reflected pulses, whereby changes between the generated and reflected pulses and in the elapsed propagation times thereof can be determined as a measure of the scouring at the structural member resulting from shifting of sediment and other materials in the floor of the body of water.

2. Apparatus as defined in claim 1, wherein said reflected pulses are a time-domain function of the relative dielectric constants of the surrounding media through which said sensor means passes.

3. Apparatus as defined in claim 2, wherein said pulse generator means and said signal analyzer means are portable and capable of being periodically connected with said sensor means, thereby allowing economical sharing of said pulse generator and signal analyzer means between numerous structural members.

4. Apparatus as defined in claim 3, and further comprising a coaxial transmission line connecting said pulse generator and signal analyzer means to said sensor means.

5. Apparatus as defined in claim 4, wherein said coaxial transmission line is arranged within the structural member and exits through said lower portion beneath the floor of the body of water, said coaxial transmission line being connected with said sensor means which extend upward from adjacent said lower portion, said sensor means comprising a robust set of vertical transmission lines.

6. Apparatus as defined in claim 2, wherein said sensor means comprises a plurality of pairs of parallel transmission lines, and further comprising multiplexing means connected between said sensor means and said pulse generator and signal analyzer means for monitoring said plurality of said pairs of parallel transmission lines with a single of said pulse generating means and said signal analyzing means.

7. Apparatus as defined in claim 6, wherein said plurality of pairs of parallel transmission lines are positioned parallel to the structural member in areas where scouring is likely to occur, said transmission lines extending downwardly from said upper portion to adjacent said lower portion of the structural member.

8. Apparatus as defined in claim 2, wherein said signal analyzer means includes a memory means for storing a plurality of measurements of scouring at the structural member.

9. Apparatus as defined in claim 8, wherein said signal analyzer means farther includes a comparator means for calculating a change over time between said stored measurements of scouring at the structural member.

10. Apparatus as defined in claim 9, wherein said comparator means calculates said change over time in said stored measurements of scouring between an initial reference measurement and a subsequent measurement of scouring at the structural member.

11. Apparatus as defined in claim 9, wherein said signal analyzing means further includes an alarm, said alarm being triggered if said change over time between said stored measurements of scouring is greater than a predetermined threshold.

* * * * *